United States Patent [19]

Yahata et al.

[11] Patent Number: 5,034,970
[45] Date of Patent: Jul. 23, 1991

[54] FRAME STRUCTURE FOR CT SCANNER

[75] Inventors: Mitsuru Yahata; Hidehiro Fujita, both of Tochigi, Japan

[73] Assignee: Kabushiki Kaisha Toshiba, Kawasaki, Japan

[21] Appl. No.: 451,008

[22] Filed: Dec. 15, 1989

[30] Foreign Application Priority Data

Dec. 16, 1988 [JP] Japan .............................. 63-316245

[51] Int. Cl.⁵ ............................................. H05G 1/60
[52] U.S. Cl. ........................................ 378/20; 378/69; 378/68; 378/15; 378/195; 378/197; 378/208; 378/196
[58] Field of Search ................... 378/20, 11, 15, 4, 21, 378/68, 69, 195, 196, 197, 208, 209, 193

[56] References Cited

U.S. PATENT DOCUMENTS

| 4,150,292 | 4/1979 | Ter-Pogossian | 378/20 |
| 4,296,329 | 10/1981 | Mirabella | 378/20 |
| 4,789,929 | 12/1988 | Nishimura et al. | 378/20 |
| 4,916,718 | 4/1990 | Manring | 378/4 |
| 4,928,283 | 5/1990 | Gordon | 378/20 |

Primary Examiner—Constantine Hannaher
Assistant Examiner—Don Wong
Attorney, Agent, or Firm—Oblon, Spivak, McClelland, Maier & Neustadt

[57] ABSTRACT

A frame structure for a CT scanner, in which a dome for containing a scanner for an object or subject to be examined has an imaging space in its central portion, and a bed plate support mechanism carries the subject, and in which a bed plate slidably drive mechanism moves the bed plate into or out of the imaging space of the dome, and the bed plate support mechanism and the bed plate slidably drive mechanism are integrally provided to the dome.

8 Claims, 5 Drawing Sheets

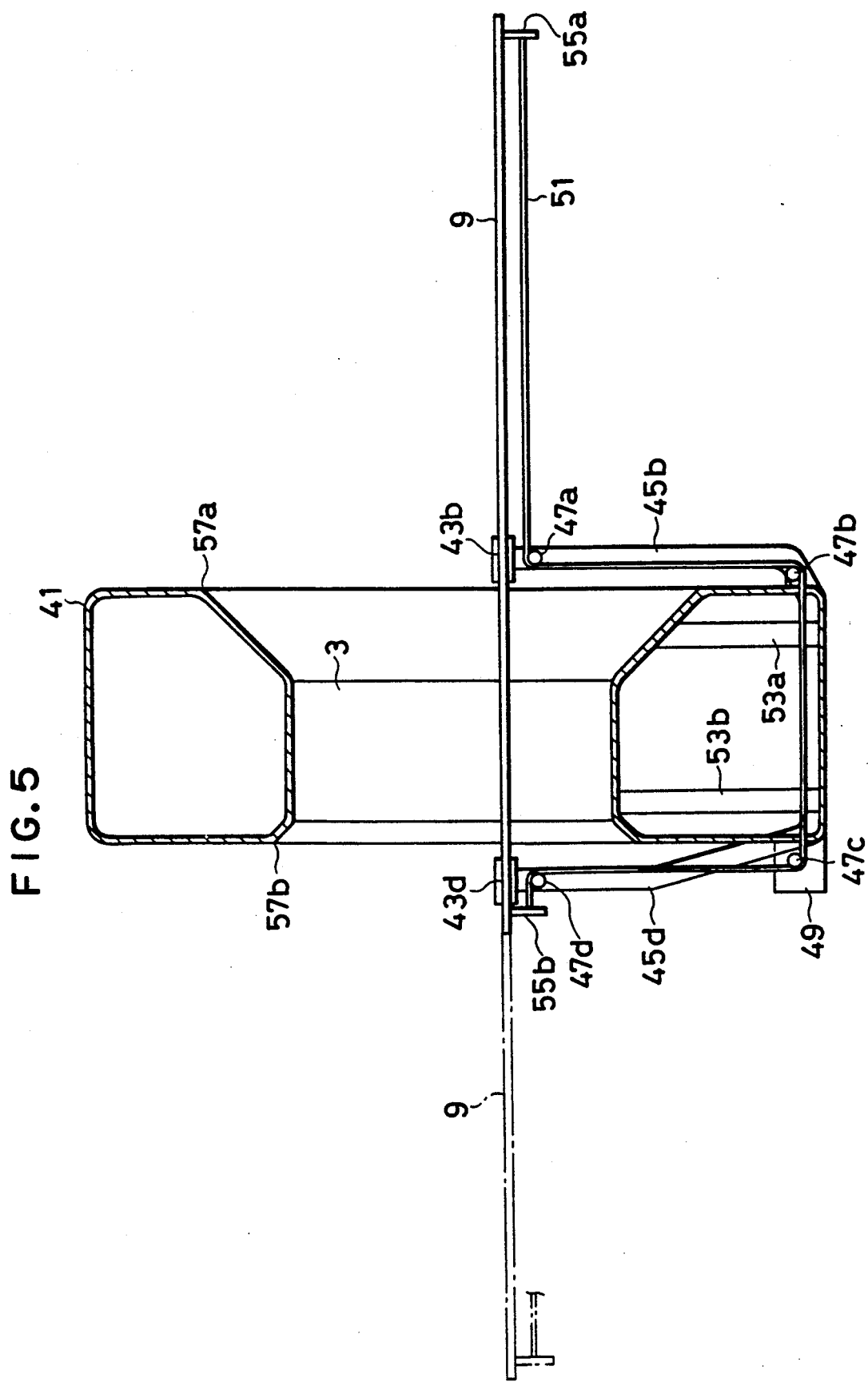

FRAME STRUCTURE FOR CT SCANNER

BACKGROUND OF THE INVENTION

1. Field of the Invention

The present invention relates to a frame structure for an X-ray CT or MRI CT scanner.

2. Description of the Background Art

In a conventional frame structure for CT scanner such as an X-ray CT scanner, an X-ray tube and an X-ray detector for scanning an object or subject in order to obtain sectional information thereof are provided in a frame dome having an imaging space therein, and a bed unit having a bed plate for carrying the subject is separately installed beside the dome. The bed plate carrying the subject is slidably moved into or out of the imaging space of the dome by a bed plate slide driver provided within the bed unit during the imaging operation of the subject, and the height of the bed plate is adjusted by a lift provided within the bed unit. In this case, the dome including the scanning apparatus and the bed unit for carrying the subject to be moved into or out of the imaging space of the dome can be independently designed and fabricated. However, the following problems arise.

That is, when the imaging of the subject is carried out by scanning the whole subject from the head to leg, the bed plate holding the subject is projected the length of the subject from the bed unit into the imaging space in the dome. Hence, the bed plate should have a sufficient strength for supporting the subject, and the bed unit should also have a sufficient strength for withstanding the prejudiced load due to the projection of the bed plate from the bed unit. Accordingly, the size and weight of the bed unit become inevitably large. Further, since the CT scanner is composed of the two units, when the CT scanner is installed, the alignment of the two units is required. That is, as described above, in this case, the large space is required for the installation of the dome and the bed unit, and the bringing and installing works of the CT scanner in an examination room are troublesome.

SUMMARY OF THE INVENTION

Accordingly, it is an object of the present invention to provide a frame structure for a CT scanner, free from the aforementioned defects and disadvantages of the prior art, which is capable of reducing and saving an installation space of the CT scanner and reducing bringing and installing works of the CT scanner in an examination room.

In accordance with one aspect of the present invention, there is provided a frame structure of a CT scanner, comprising a dome having an imaging space, for containing means for scanning an object to be examined, means for supporting a bed plate for carrying the object thereon, and means for slidably driving the bed plate into or out of the imaging space of the dome, the supporting means and the driving means being integrally provided to the dome.

BRIEF DESCRIPTION OF THE DRAWINGS

The above and other objects, features and advantages of the present invention will more fully appear from the following description of the preferred embodiments with reference to the accompanying drawings, in which:

FIG. 5 is a central longitudinal cross section of the frame structure shown in FIG. 4.

DESCRIPTION OF THE PREFERRED EMBODIMENTS

Figure 1:
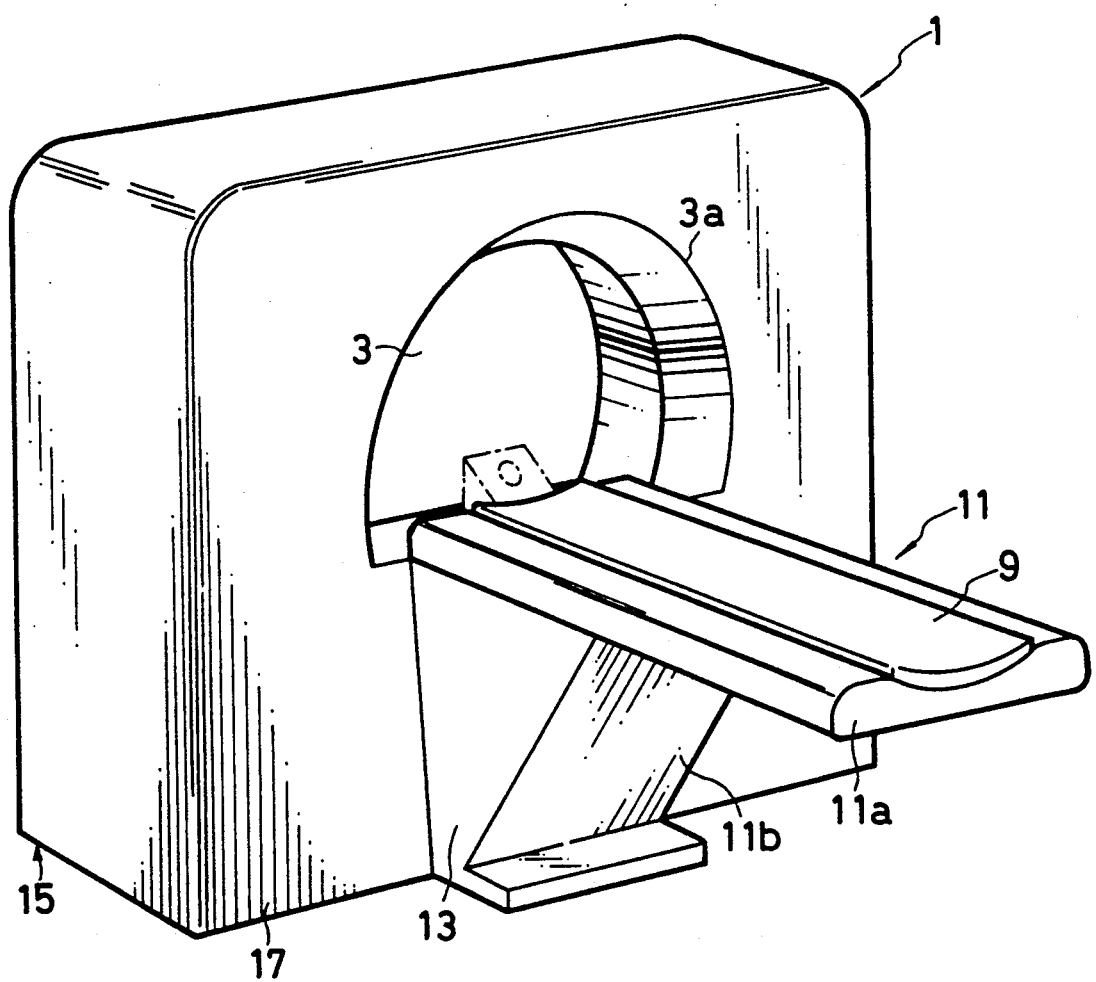
FIG. 1 is a perspective view of a first embodiment of a frame structure for a CT scanner according to the present invention.
Figure 2:
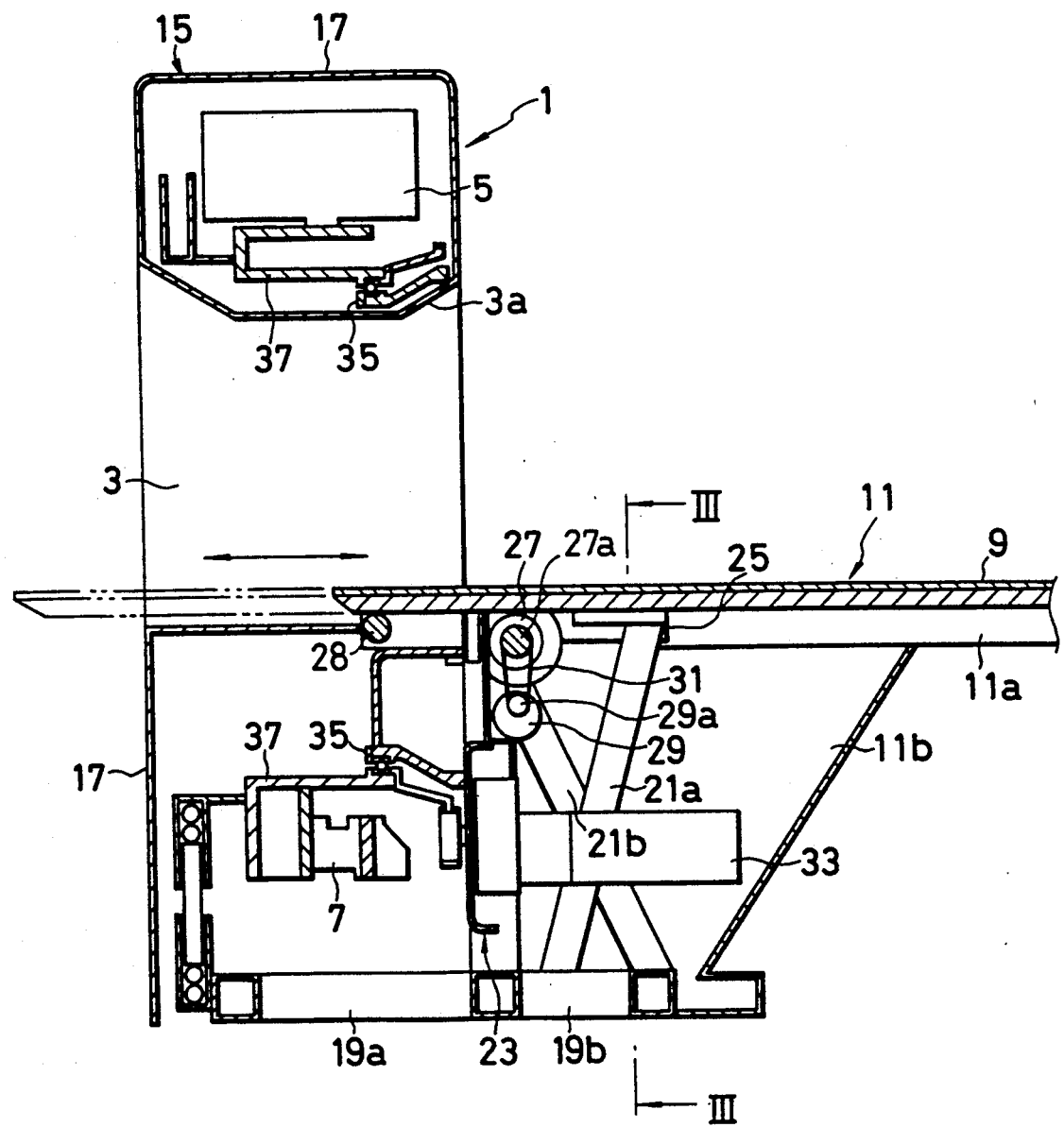
FIG. 2 is a central longitudinal cross section of the frame structure shown in FIG. 1.
Figure 3:
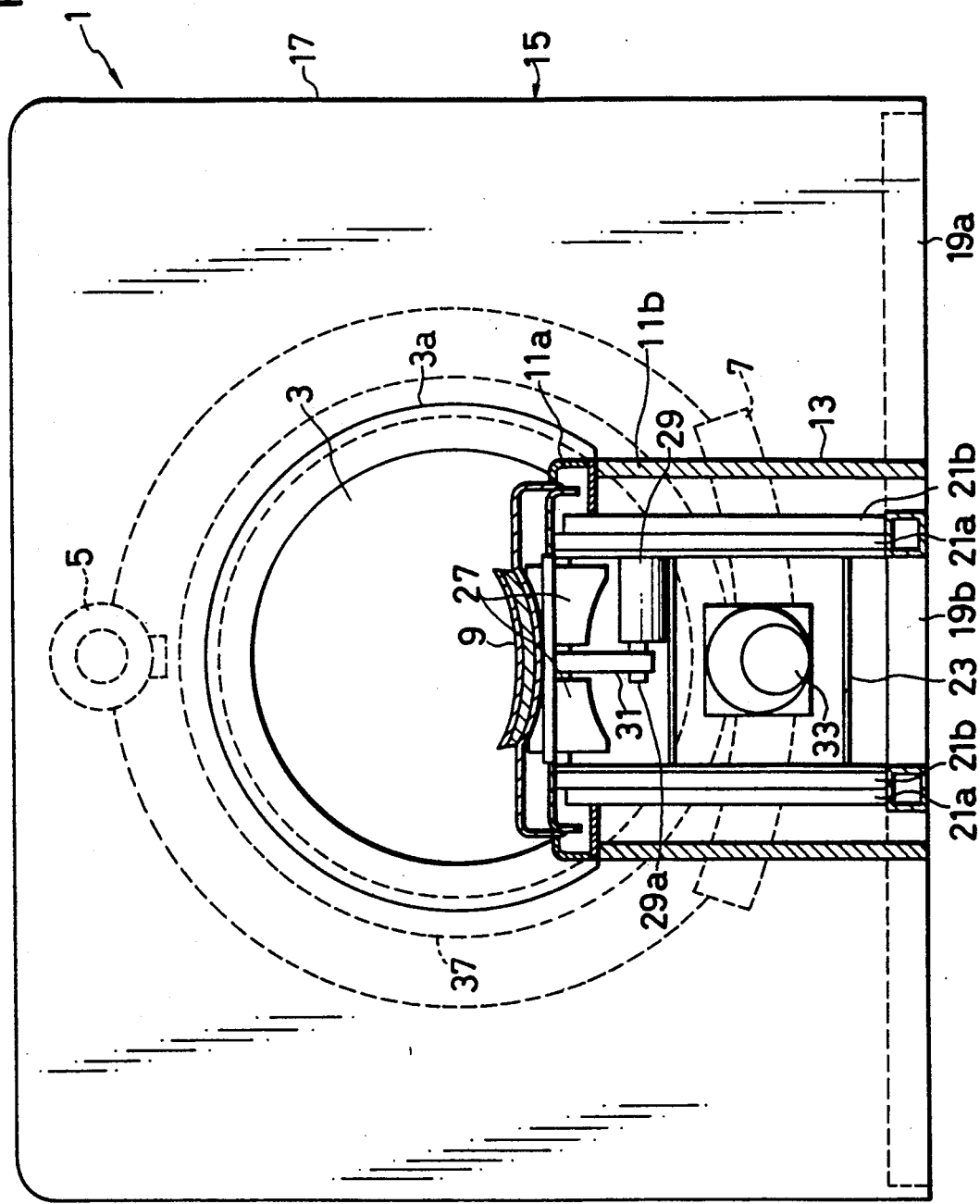
FIG. 3 is a longitudinal cross sectional view, taken along the line III—III in FIG. 2.

Referring now to the drawings, wherein like reference characters designate like or corresponding members throughout the several views and thus the repeated description thereof may be ommited for the brevity, there is shown in FIGS. 1 to 3 the first embodiment of a frame structure for a CT scanner such as an X-ray CT scanner or a MRI CT scanner according to the present invention.

In the drawings, a frame structure 1 for a CT scanner comprises a dome section 15 having an imaging space 3 of a semicylinder-like form in its center and a bed section 11 integrally connected to the front end of the dome section 15 and projecting frontwards from the bottom portion of the imaging space 3. An X-ray tube 5 and an X-ray receiver or detector 7 are so mounted to a rotary ring member 37 arranged within the dome section 15 as to position in opposite sides of the imaging space 3 and to face to each other. As the rotary ring member 37 is rotated around the imaging space 3, the X-ray tube and detector 5 and 7 are revolved around the imaging space 3. The X-ray tube 5 radiates the X-ray in a sectorial shape towards the X-ray detector 7, and the X-ray detector 7 receives the radiated X-ray to obtain signals which are processed to reproduce a sectional image of an object or subject (not shown) on a display.

The bed section 11 is composed of a projection portion 11a for carrying a slidable bed plate 9 for supporting a subject (not shown) to be scanned and a support portion 11b, provided below the projection portion 11a, having an inverted rectangular cone form for supporting the bottom of the projection portion 11a. The support portion 11b is covered by a cover 13, and the dome section 15 is covered by another cover 17. The covers 13 and 17 are integrally and continuously formed, and thus the cover 13 for the support portion 11b also covers the lower front end portion of a spreading front opening 3a of the dome section 15.

The dome section 15 is provided with a bottom support member 19a in its bottom, and the support portion 11b of the bed section 11 is also provided with a bottom support member 19b in its bottom. The rear end of the bottom support member 19b of the support portion 11b is connected to the front end of the bottom support member 19a of the dome section 15. Two pairs of pillars 21a and 21b, each pair constituting an X-shaped support member, erect from the bottom support member 19b in its left and right side end portions, and the top ends of the pillars 21a and 21b are linked to the projection portion 11a of the bed section 11. A support plate 23 is vertically mounted to the lower front end of the dome section 15 at the coupling portion between the dome section 15 and the support portion 11b.

The projection portion 11a is formed with a cutout 25 in its central rear end portion. A pair of rollers 27 are rotatably mounted between the left and right pillars 21b through a shaft 27a in the cutout 25 of the projection portion 11a so as to contact with the bottom of the bed plate 9 slidably held on the projection portion 11a. A motor 29 having a rotary shaft 29a is secured to the pillar 21b, and a belt 31 is extended between the shaft 27a of the rollers 27 and the rotary shaft 29a of the motor 29. An idler roller 28 for supporting the bed plate 9 is rotatably mounted in the dome section 15 to extend in the left and right side direction at the same height as the projection portion 11a of the bed section 11. Thus, by driving the motor 29, the rollers 27 are rotated in the desired direction to slidably move the bed plate 9 into or out of the imaging space 3 of the dome section 15 in the frontward or rearward direction, as shown by two dotted lines in FIG. 2.

Another motor 33 is mounted to the front side of the support plate 23 for driving the rotary ring member 37 which is rotatably mounted to the dome section 15 through a roll bearing 35 and to which the X-ray tube 5 and the X-ray detector 7 are mounted, as described above.

In this embodiment, as described above, the dome section 15 includes the semicylindrical imaging space 3 therein, and the bed section 11 including the projection portion 11a for holding the slidable bed plate 9 thereon and the support portion 11b are integrally provided on the lower front end of the dome section 15. The rollers 27 contacting with the bottom of the bed plate, the shaft 27a of the rollers 27, the motor 29 having the rotary shaft 29a for driving the rollers 27 and the belt 31 for transmitting the rotary force of the motor 29 to the shaft 27a constitute a bed plate slide drive mechanism arranged within the support portion 11b of the bed section 11. The motor 33 for driving the rotary ring member 37 is also arranged within the support portion 11b of the bed section 11. The X-ray tube 5, the X-ray detector 7, the rotary ring member 37 holding the X-ray tube and detector 5 and 7, the roller bearing 35 and the motor 33 constitute the scanning apparatus arranged within the dome section 15.

Consequently, in this embodiment, as compared with a conventional frame structure for a CT scanner composed of the separated frame dome and the bed unit including a bed plate slide mechanism and a bed plate lift mechanism, the bed section 11 is integrally coupled to the dome section 15 to reduce the size and space of the entire frame structure, and the motor 33 for driving the rotary ring member 37 carrying the X-ray tube 5 and the X-ray detector 7 thereon is moved from the dome section 15 to the support portion 11b of the bed section 11 to reduce the size such as the thickness in the front and rear direction and the space of the dome section 15, thereby obtaining a compact and slender frame structure for a CT scanner having no useless space therein.

Further, the number of the parts for fabricating the frame structure and the fabricating steps can be reduced to lower the producing cost. Also, the installation space can be saved, and the installation work such as the bringing and installing of the frame structure in an examination room without any alignment work, and the anchoring of the frame structure on the floor, and the number of the anchors for use in the anchoring can be reduced. In this case, since the bed section is integrally coupled to the dome section, electric wiring such as electric cables and cords for use in the bed section can be suitably mounted within the frame structure, and thus the wiring work and the wiring space can be largely reduced or omitted.

In this embodiment, although a conventional frame dome has a cylindrical imaging space with a circular opening, whose lower space is usually useless, the dome section of the present invention is formed with a semi-cylinder-like imaging space above the bed plate in order to save the lower space of the cylindrical imaging space of the conventional dome, thereby obtaining a compact and slender frame structure having no useless space therein.

Figure 4:
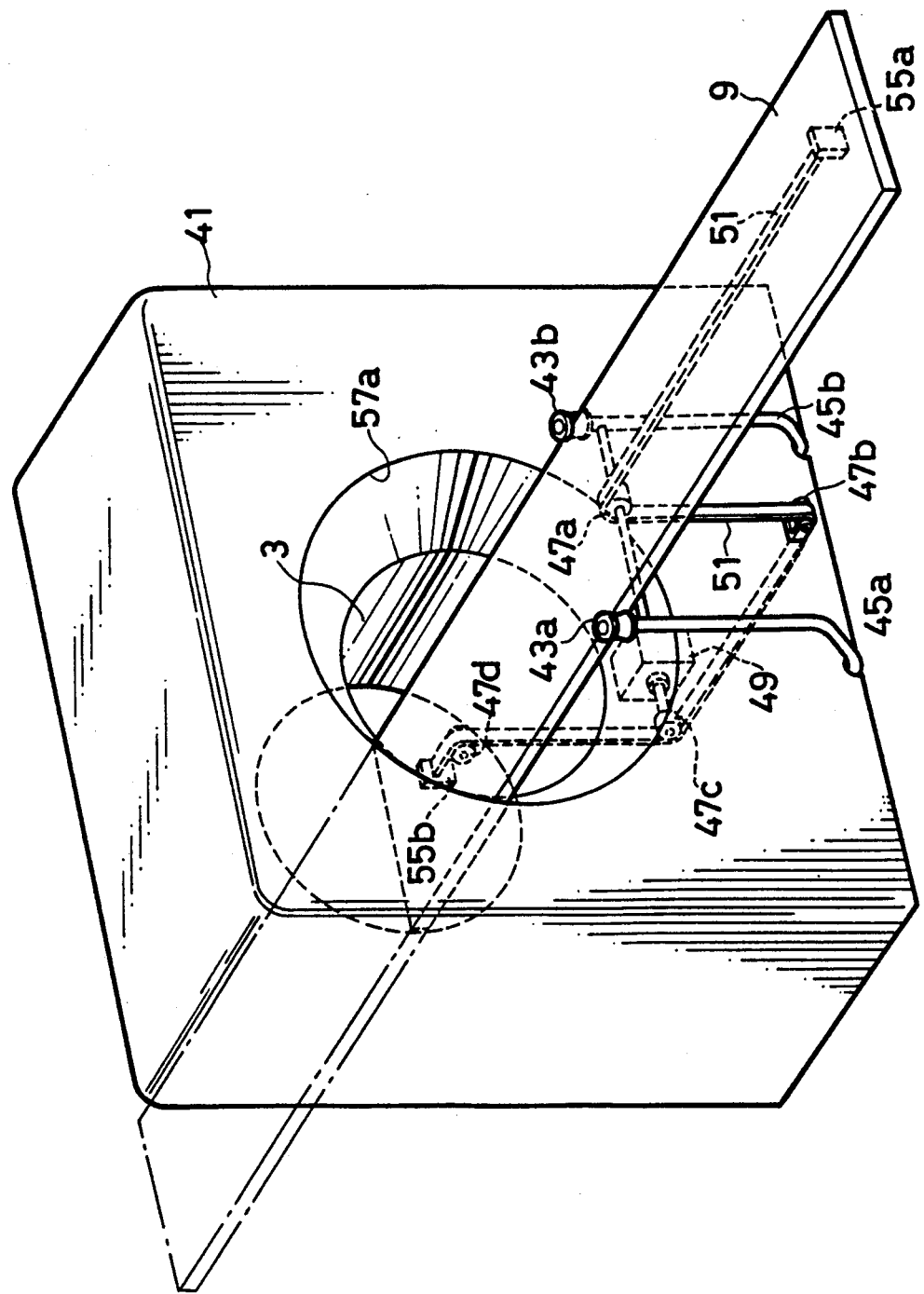
FIG. 4 is a perspective view of a second embodiment of a frame structure for a CT scanner according to the present invention.

In FIGS. 4 and 5, there is shown the second embodiment of a frame structure for a CT scanner according to the present invention, having a similar structure to that of the first embodiment shown in FIGS. 1 to 3, except a bed plate sliding mechanism instead of the bed section 11 of the first embodiment.

In this embodiment, a dome section 41 is provided with an imaging space 3 of a cylinder-like form in its center. Four pillars 45a, 45b, 45c and 45d so stand from the front and rear bottom ends in the lower central front and rear portions of the dome section 41 that the width between the left front and rear pillars 45a and 45c and the right front and rear pillars 45b and 45d is determined to be approximately equal to that of the bed plate 9 for carrying the subject (not shown) thereon. Four support rollers 43a, 43b, 43c and 43d having a horizontal groove are rotatably mounted to the top ends of the respective pillars 45a, 45b, 45c and 45d, and the bed plate 9 is slidably mounted on the left and right sides by the four support rollers 43a, 43b, 43c and 43d at their grooves.

Two sprocket wheels 47a and 47d are rotatably mounted to the central front intermediate and rear intermediate end portions through shafts horizontally extended between the pairs of front and rear pillars 45a, 45b, 45c and 45c outside the dome section 41 near front and rear spreading openings 57a and 57b of the imaging space 3 right under the bed plate 9, and the other two sprocket wheels 47b and 47c are rotatably mounted to the central front and rear bottom end portions outside the dome section 41. A rotary shaft of a drive motor 49 is coupled to the sprocket wheel 47c. A pair of front and rear stoppers 55a and 55b are mounted to the central front and rear bottom end portions of the bed plate 9, and a chain 51 is extended between the front and rear stoppers 55a and 55b through the four sprocket wheels 47a, 47b, 47c and 47d so as to make a detour round the peripheral portion of the dome section 41 without passing through the imaging space 3 in order to prevent the interruption of the X-ray path between the X-ray tube and the X-ray detector.

Hence, by driving the motor 49, the four sprocket wheels 47a to 47d are rotated in the desired direction to slidably move the chain 51 and thus the bed plate 9 carrying the subject thereon into or out of the imaging space 3 of the dome section 41 in the frontward or rearward direction. Support pillars 53a and 53b are provided in the front and rear end portions of the dome section 41, and are connected to the pillars 45a to 45d for reinforcing the bed plate supporting force thereof.

In this embodiment, the four support rollers 43a to 43d and the four pillars 45a to 45d constitute a bed plate support mechanism, and the four sprocket wheels 47a to 47d, the drive motor 49, the chain 51 and the stoppers 55a and 55b constitute a bed plate slide drive mechanism.

In this embodiment, although the bed plate 9 is held on the left and right sides at the four portions by the four rollers 43a to 43d, however, each pair 43a and 43c or 43b and 43d of the left and right side rollers is integrally coupled to each other to form a single support device so that the bed plate 9 can be held on the left and right sides at the two portions by the left and right single support devices. The four pillars 45a to 45d may be provided within the dome section 41. The rotary shaft of the motor 49 may be coupled with another sprocket wheel 47a, 47b or 47d instead of the sprocket wheel 47c or a particular sprocket wheel engaging with the chain 51. Further, the motors for driving the bed plate 9 and the rotary ring member for supporting the X-ray tube and the X-ray detector may be arranged under the bed plate and be covered by a cover member in the same manner as the first embodiment described above. In this embodiment, the same effects and advantages as those of the first embodiment can be obtained.

Although the present invention has been described in its embodiments applied to an X-ray CT scanner, it is readily understood that, of course, a frame structure for a CT scanner according to the present invention can be applied to a MRI CT scanner.

As described above, according to the present invention, the bed plate support mechanism and the bed plate sliding mechanism are integrally coupled to the dome section to reduce the size and space of the entire frame structure, and the strength for withstanding the prejudiced load due to the projection of the bed plate from the bed plate support mechanism into the imaging space is reduced to diminish the weight of the frame structure. The installation space can be saved, and the installation work such as the bringing and installing of the frame structure in an examination room without any alignment work can be reduced. In the frame structure of the present invention, since no lift for adjusting the height of the bed plate is required to save the space under the bed plate, the motor for driving the rotary ring member supporting the X-ray tube and the X-ray detector thereon is moved from the dome section to the saved space under the bed plate to reduce the size and the space of the dome section, thereby obtaining a compact and slender frame structure for a CT scanner having no useless space therein.

In a frame structure for a CT scanner according to the present invention, a chain is extended between front and rear stoppers of a bed plate through sprocket wheels rotatably mounted in central front and rear end portions near a periphery of a dome section so as to make a detour round the peripheral portion of the dome section without passing through an imaging space in order to prevent interruption of an X-ray path between an X-ray tube and an X-ray detector in an X-ray CT scanner or interruption or of magnetic field and affection to the magnetic field in a MRI CT scanner.

In the above described embodiments of the frame structure for the CT scanner according to the present invention, the dome section is not slanted with respect to the bed plate, and hence only sectional data of the subject with a fixed sectional angle is obtained. However, the obtained sectional data with the fixed sectional angle can be processed to obtain sectional data with variable sectional angles in a conventional manner.

Although the present invention has been described in its preferred embodiments with reference to the accompanying drawings, it is readily understood that the present invention is not restricted to the preferred embodiments and that various changes and modifications can be made by those skilled in the art without departing from the spirit and scope of the present invention.

What is claimed is:

1. A frame structure for a CT scanner, comprising:
   a dome having an imaging space, for containing means for scanning an object to be examined;
   a bed section having a slidable bed plate for supporting the object, a projection portion for carrying the slidable bed plate, and a support portion for supporting the projection portion; and
   supporting means having a first support member for supporting the dome, and a second support member for supporting the bed section, said first and second support members being fixedly interconnected to provide a common support for said dome and said bed section;
   whereby said dome and said bed section are constructed as a single unit.

2. The structure of claim 1, comprising:
   a driver for driving a rotary ring member for carrying the scanning means arranged under the bed plate.

3. The structure of claim 2, wherein the scanning means includes a radiant source and a detector therefor.

4. The structure of claim 1, wherein the imaging space has a semicylinder-like form and is formed above the slidable bed plate, and wherein the dome is covered by a first cover and a lower side of the bed plate is covered by a second cover, the first and second covers being integrally and continuously formed.

5. The structure of claim 1, further comprising:
   means for slidably driving the slidable bed plate into or out of the imaging space of the dome.

6. The structure of claim 5, wherein the driving means includes roller means contacting with the bottom of the bed plate and a driver arranged near the dome for driving the roller means.

7. The structure of claim 5, wherein the supporting means includes pillars standing from the bottom of the dome and at least two support devices mounted to the top end portions of the pillars, for supporting left and right sides of the bed plate, and wherein the driving means includes sprocket wheel means rotatably mounted near peripheral portions of the dome under the bed plate, a driver for driving one of the sprocket wheel means, and a chain extended between the front and rear lower end portions of the bed plate through the sprocket wheel means.

8. The structure of claim 7, wherein the sprocket wheel means include at least three sprocket wheels arranged near the peripheral portions of the dome under the bed plate.

* * * * *